(12) United States Patent
Maskin

(10) Patent No.: US 10,159,599 B2
(45) Date of Patent: Dec. 25, 2018

(54) MEIBOMIAN GLAND INTRADUCTAL DIAGNOSTIC AND TREATMENT METHODS

(75) Inventor: Steven L. Maskin, Tampa, FL (US)

(73) Assignee: MGD INNOVATIONS, LLC, Tampa, FL (US)

( * ) Notice: Subject to any disclaimer, the term of this patent is extended or adjusted under 35 U.S.C. 154(b) by 1883 days.

(21) Appl. No.: 12/305,094

(22) PCT Filed: Nov. 13, 2008

(86) PCT No.: PCT/US2008/083318
§ 371 (c)(1),
(2), (4) Date: Dec. 16, 2008

(87) PCT Pub. No.: WO2009/064834
PCT Pub. Date: May 22, 2009

(65) Prior Publication Data
US 2010/0292630 A1  Nov. 18, 2010

Related U.S. Application Data

(60) Provisional application No. 60/987,521, filed on Nov. 13, 2007.

(51) Int. Cl.
*A61M 31/00* (2006.01)
*A61F 9/00* (2006.01)
*A61F 9/007* (2006.01)

(52) U.S. Cl.
CPC ........ *A61F 9/0017* (2013.01); *A61F 9/00709* (2013.01)

(58) Field of Classification Search
CPC .............................. A61F 9/0017; A61F 9/007
(Continued)

(56) References Cited

U.S. PATENT DOCUMENTS 3,834,391 A * 9/1974 Block .................. A61B 18/203
                                              385/115
4,211,767 A * 7/1980 Klein .................... A61K 8/4953
                                              424/184.1
(Continued)

FOREIGN PATENT DOCUMENTS

| JP | 11-221247 | 8/1999 |
|----|-----------|--------|
| WO | 9404155 | 3/1994 |
| WO | 2008076544 | 6/2008 |

OTHER PUBLICATIONS

Reinstein et al. Successful treatment of distichiasis in a cat using transconjunctival electrocautery; Veterinary Ophthalmology (2011) 14 Supplement 1, 130-134.*

(Continued)

*Primary Examiner* — Deanna K Hall
(74) *Attorney, Agent, or Firm* — Allen Dyer Doppelt & Gilchrist

(57) ABSTRACT

A method is provided for treating a meibomian gland of an eyelid of a patient. In a particular embodiment, an obstruction in a meibomian gland and the orifice thereof can be alleviated; in another, a substance can be injected thereinto; in yet another, the gland can be aspirated. The method includes the step of inserting an elongated probe into a meibomian gland via an orifice thereinto. In some embodiments the probe can have a longitudinal lumen therethrough, with at least one distal hole through the probe wall in fluid communication with the lumen. The lumen can be used in concert with a source of suction for removing debris from the meibomian gland, and/or with a source of a fluid and pumping means, for injecting a substance into the meibomian gland.

25 Claims, 12 Drawing Sheets

(58) Field of Classification Search
USPC ........ 604/173, 521, 506, 289, 294, 298, 300
See application file for complete search history.

(56) References Cited

U.S. PATENT DOCUMENTS

| | | | |
|---|---|---|---|
| 4,583,539 A * | 4/1986 | Karlin | A61B 18/20 |
| | | | 219/121.74 |
| 4,915,684 A * | 4/1990 | MacKeen | A61F 9/00772 |
| | | | 604/264 |
| 5,283,063 A * | 2/1994 | Freeman | 424/427 |
| 6,235,016 B1 * | 5/2001 | Stewart | A61B 18/203 |
| | | | 606/13 |
| 6,344,047 B1 | 2/2002 | Price et al. | |
| 6,428,502 B1 | 8/2002 | Lang | |
| 6,936,053 B1 | 8/2005 | Weiss | |
| 7,211,070 B2 | 5/2007 | Soroudi | |
| 7,678,065 B2 * | 3/2010 | Haffner | A61B 3/16 |
| | | | 600/398 |
| 2002/0116750 A1 | 8/2002 | Korb | |
| 2003/0072711 A1 | 4/2003 | Korb | |
| 2003/0211043 A1 | 11/2003 | Korb | |
| 2004/0237969 A1 | 12/2004 | Fuller | |
| 2006/0058743 A1 * | 3/2006 | Putz | 604/264 |
| 2006/0153885 A1 | 7/2006 | Korb et al. | |
| 2006/0270621 A1 * | 11/2006 | Christiano | A61K 9/0014 |
| | | | 514/44 R |
| 2007/0016254 A1 | 1/2007 | Grenon et al. | |
| 2007/0016255 A1 | 1/2007 | Korb et al. | |
| 2007/0016256 A1 * | 1/2007 | Korb | A61F 9/00772 |
| | | | 607/1 |
| 2007/0027431 A1 | 2/2007 | Korb et al. | |
| 2007/0036726 A1 | 2/2007 | Korb | |
| 2007/0260201 A1 | 11/2007 | Prausnitz et al. | |
| 2008/0081999 A1 * | 4/2008 | Gravely et al. | 600/473 |

OTHER PUBLICATIONS

H.W. Cowper, Meibomian Seborrhea, American Journal of Opthalmology, vol. 5, Iss. 1, Jan. 1922, pp. 25-30.*
PCT International Search Report for PCT/US2008/083318 dated Jun. 11, 2009, pp. 1-4.
Supplemental European Search Report dated Oct. 29, 2010 in relation to European Application No. 08850779.3, sheets 1-3.

* cited by examiner

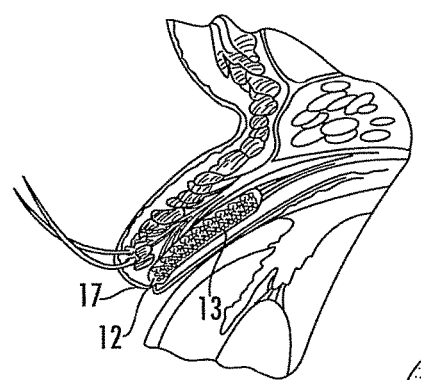
FIG. 5
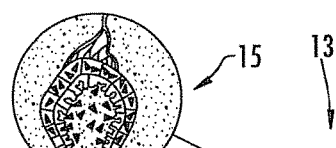
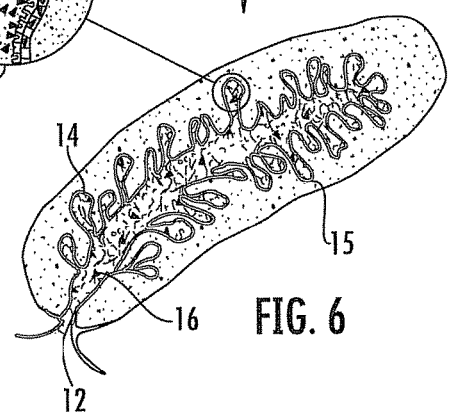
FIG. 6
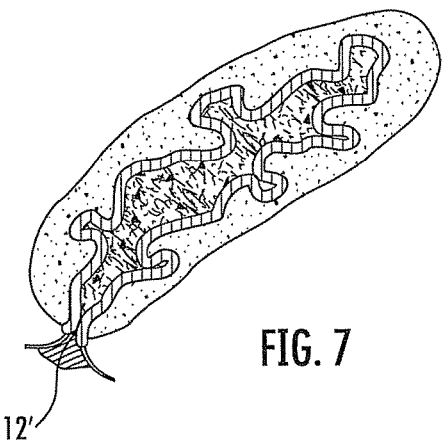
FIG. 7

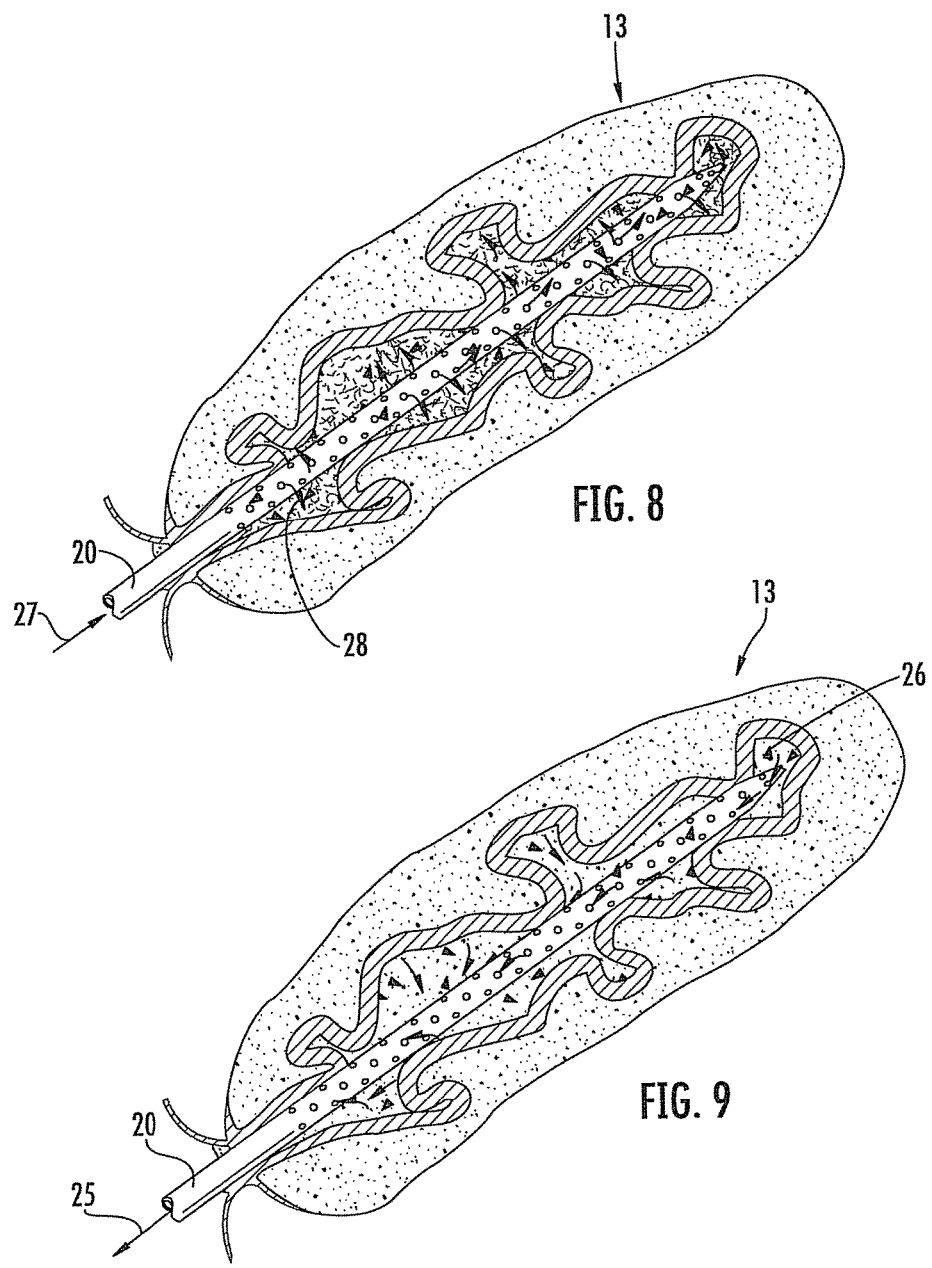

MEIBOMIAN GLAND INTRADUCTAL DIAGNOSTIC AND TREATMENT METHODS

CROSS-REFERENCE TO RELATED APPLICATION

This application is the § 371 National Stage of International Application No. PCT/US08/083318, filed on Nov. 13, 2008, which claims the benefit of U.S. Provisional Application Ser. No. 60/987,521, filed on Nov. 13, 2007, the contents of which applications are hereby incorporated by reference in their entirety.

FIELD OF THE INVENTION

The present invention relates to systems, devices, and methods for treating and diagnosing ailments of the meibomian gland, such as removing obstructions or other types of material from, and adding material such as medication into, the meibomian gland.

BACKGROUND OF THE INVENTION

"Dry eye syndrome" can be caused by, among other things, obstructions in the meibomian gland, preventing lipid secretions from reaching the surface of the eye. These lipid secretions, in a healthy eye, form the outer layer of the tear film, and thereby assist in reducing tear evaporation during waking hours.

Currently, dry eye syndrome is treated, depending upon the severity, with over-the-counter preserved tears, topical and systemic medications, and even surgery. The patient's environment, dietary habits, and medications are considered and can be addressed if thought to be a factor in producing patient's dry eye syndrome.

However, at present there is no effective way of removing obstructions within the meibomian gland, and therefore it would be desirable to provide a system, device, and method for doing so.

SUMMARY OF THE INVENTION

The present invention is directed to a system, device, and method for treating a meibomian gland of an eyelid of a patient. In a particular aspect, an obstruction in a meibomian gland and the orifice thereof can be alleviated; in another, a substance can be injected thereinto; in yet another, the gland can be aspirated.

The method comprises inserting an elongated probe into a meibomian gland via an orifice thereinto. In some aspects the probe can have a longitudinal lumen therethrough, with at least one distal hole through a probe wall in fluid communication with the lumen. The lumen can be used in concert with a source of suction for removing debris from the meibomian gland, and/or with a source of a fluid and pumping means, for injecting a substance into the meibomian gland.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 5 is a side cross-sectional view of an eyelid, including a meibomian gland.

FIG. 6 is a side cross-sectional view of a meibomian gland and a detailed view of an acinar complex.

FIG. 7 is a cross-sectional view of an obstructed meibomian gland.

FIGS. 8 and 9 are side cross-sectional views of a meibomian gland with a probe inserted thereinto and injecting a pharmacological agent (FIG. 8) and performing aspiration (FIG. 9).

DETAILED DESCRIPTION OF PREFERRED EMBODIMENTS

Figure 1:
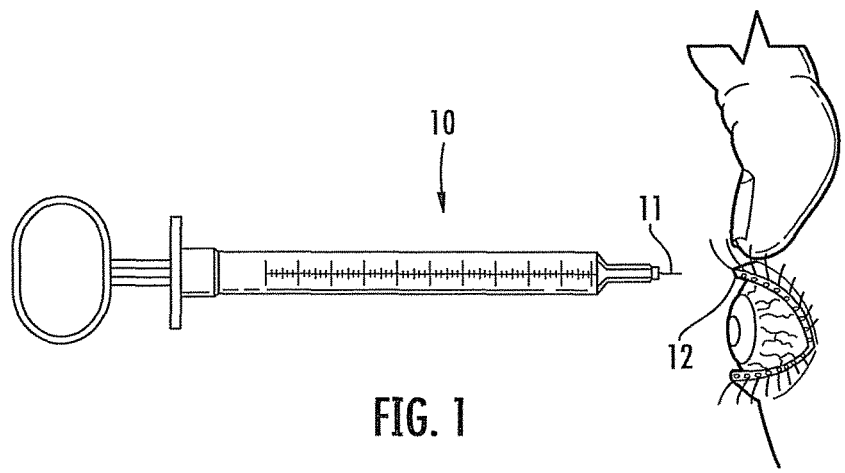
FIG. 1 is a side perspective view of a probe being inserted into a meibomian gland of an eyelid of a patient.
Figure 2:
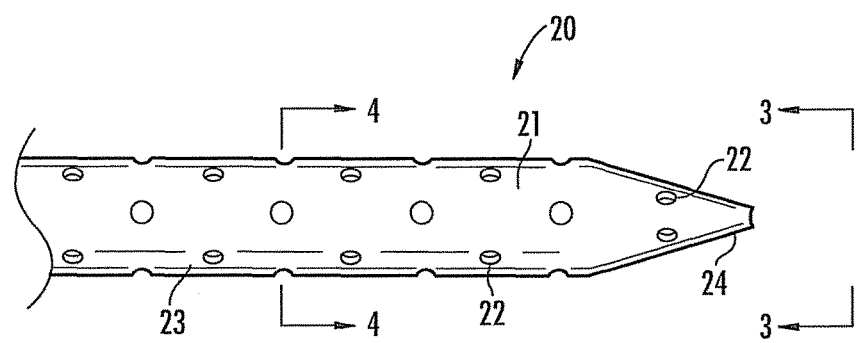
FIG. 2 is a side perspective view of a probe having apertures into a lumen.
Figure 3:
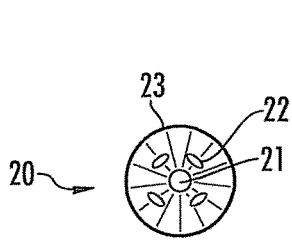
FIGS. 3 and 4 are cross-sectional views of the probe of FIG. 2 along lines 3-3 and 4-4, respectively.
Figure 4:
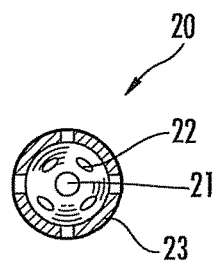
Figure 10:
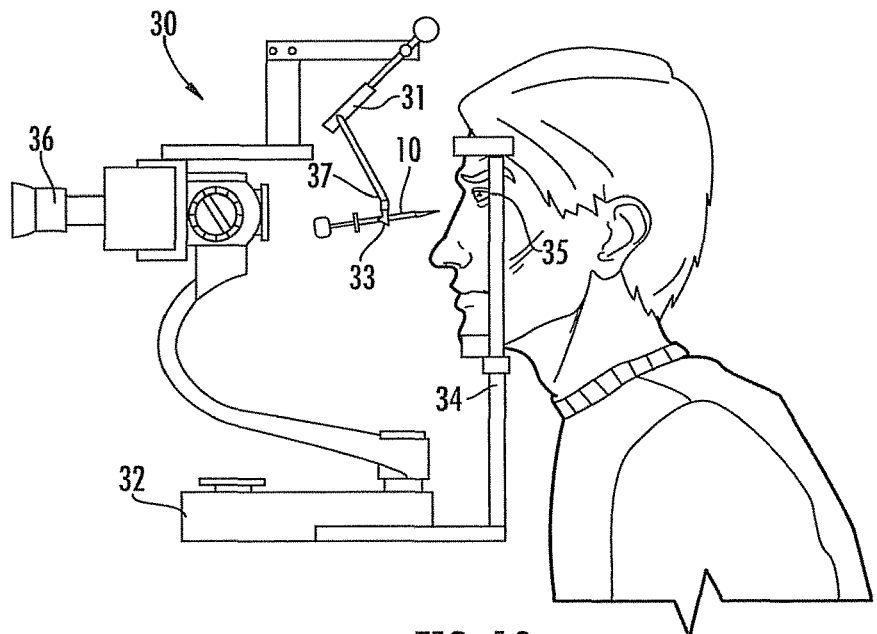
FIG. 10 is a side perspective view of an instrument for supporting a probe.

A description of the preferred embodiments of the present invention will now be presented with reference to FIGS. 1-29.

The system, device, and method for treating a meibomian gland of an eyelid of a patient can include the use of a probe to perform a plurality of procedures, such as, but not intended to be limited to, alleviating an obstruction therein. The present inventor has found that the meibomian gland can be successfully penetrated with such a probe, to clear obstructions or for other treatments, with a sufficiently thin probe. Accordingly, all embodiments entail the use of an elongated probe having a distal portion dimensioned for insertion into a meibomian gland via an orifice thereof. An exemplary probe 10 (FIG. 1) has a tip or distal end 11 dimensioned for insertion into an orifice 12 of a meibomian gland 13 (FIGS. 5-7). In basic embodiment, the distal end 11 is a thin wire fixedly secured, for instance with epoxy, to the remainder of the probe 10. The distal end 11 can be formed from stainless steel or another bio-suitable material. The probe 10 can be made to be autoclavable and re-usable, or disposable for one-time use.

The meibomian gland 13 is a modified sebaceous gland surrounded by dense collagen that produces oil droplets, waxes, and cholesterol 14 that migrate from evaginations 15 in the gland's interior space 16 toward the orifice 12 at the eyelid margin 17. The lipid secretions produced serve to stabilize tears, and there are typically approximately 24 such glands per human eyelid. An obstructed orifice 12' is illustrated in FIG. 7.

A typical gland orifice 12 has a diameter of approximately 0.1 mm. Thus, the probe 10 advantageously has distal end with an outer diameter of approximately 100 μm or less, and most advantageously approximately 50 μm to approximately 80 μm. Additionally, a typical, non-atrophied gland 13 has a depth, from the orifice 12 to a distal end 19, of approximately 4 mm to approximately 5 mm. Generally, the lower lid has shorter, wider glands than the upper lid. Thus, the probe 10 advantageously has a distal end with a length of 6 mm or less. Distal ends 11 with lengths of approximately 2 mm and approximately 4 mm are also advantageous.

Where a wider distal end is to be inserted, for example having an outer diameter closer to 100 μm, it has been found advantageous to previously insert one or more narrower distal ends, for example, 50 μm and/or 80 μm to initially clear any blockage within the orifice 12 and to relax the orifice to ease entry of the larger distal end(s). Depending on the particular circumstances, for instance the time constraints or pain tolerance of the patient, a week or more can elapse between insertion of the narrower and wider distal ends. Where a longer distal end is to be inserted, for example having a length of approximately 4 mm to 6 mm, it has been found advantageous to previously insert one or more shorter distal ends, for example, 2 mm to initially clear any blockage within the orifice 12. For distal ends of equal diameter, the shorter distal ends will generally exhibit a greater resistance to bending than the longer distal ends. Thus, the likelihood of successful insertion of longer distal ends into the meibomian glands can be enhanced with prior insertion of one or more shorter distal ends.

In practice with a probe 10, the present inventor has discovered evidence of the formation of both fibrotic bands and vascular structures with the meibomian gland central duct. The presence of fibrotic bands within the meibomian gland duct can be indicated by initial resistance to the insertion of the probe 10 that is overcome following a "pop" upon breaking through the bands. The presence of vascular structures can be indicated by the presence of a drop of blood after removing the probe 10. The routine existence of such structures within the meibomian gland duct was, to knowledge of the present inventor, previously unknown. Based on this discovery, the present invention further extends to therapeutic modalities to prevent the re-formation of such structures. Thus, treatment can be further directed at remedying the condition underlying the improper or reduced function of the meibomian gland, rather than simply clearing obstructions as they form. For instance, medicines including fibrous tissue and/or vascular tissue growth inhibiting agents, such as steroids and/or vascular endothelial growth factor (VEGF) inhibitors, can be introduced into the meibomian gland.

Subsequent to the present invention, penetration of the meibomian gland to clear obstructions has been accomplished using an instrument having an energized tip. Using plasma energy, the device effectively vaporizes obstructions, as well as any other matter, including living tissue, that comes into contact with the energized tip. Significantly, the probe 10 and related methods of use do not require the application of thermal energy, electromagnetic energy or other radiation, or other energy beyond the application of mechanical force sufficient to physically penetrate the meibomian gland. However, the present invention is not necessarily limited to purely physical penetration. Additionally, the present invention can advantageously include the application of additional energy after the probe 10 has been inserted through the orifice 12.

In addition to reducing the risk of trauma to otherwise healthy tissue, the penetration of the meibomian gland without the application of thermal or electromagnetic energy to the probe 10 facilitates the diagnosis of the potential underlying conditions described above. For instance, plasma energy would readily vaporize fibrotic bands, not allowing the surgeon to feel the indicative resistance and subsequent pop. Similarly, vascular structures would also be vaporized, and capillaries feeding the structures would likely be immediately cauterized, eliminating the blood evidence.

Figure 30:
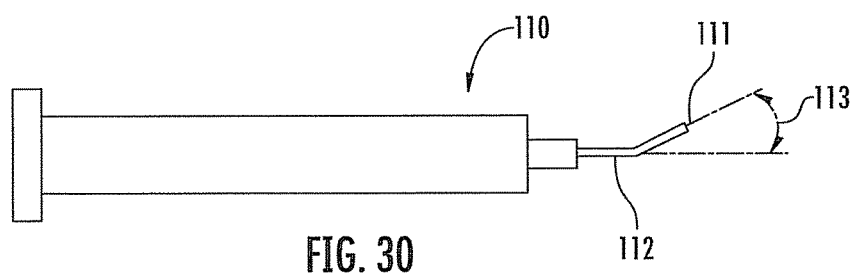
FIG. 30 is a schematic side view of a probe having a distal end connected with a bent cannula.

In another embodiment (FIG. 30), a probe 110, a distal end 111 is attached to the probe 110 by a bent cannula 112. The bent cannula 112 serves to move most of the body of the probe 110 out of the line of sight of a doctor when inserting the distal end 111 in the meibomian gland. Advantageously, the cannula is bent to an angle 113 of approximately 30 degrees.

Figure 31:
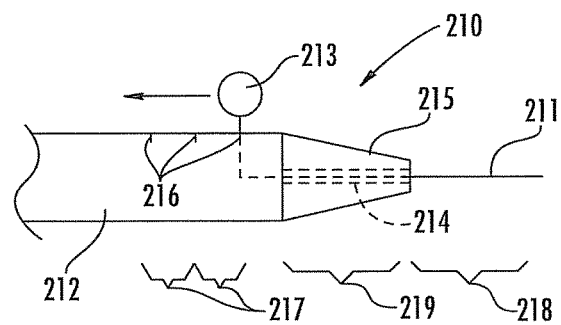
FIG. 31 is a partial schematic side view of a probe having distal end advanceable in fixed intervals, with hidden components shown in broken lines.

In a further embodiment (FIG. 31), a probe 210 has a distal end 211 that is displaceable relative to a body 212 of the probe 210. The distal end 211 is connected to an operator 213 and slidably supported in a channel 214 defined within a distal section 215 of the body 212. Using the operator 213, the distal end 211 is advanceable and retractable. Preferably, the detents 216 are formed in the body 212 to allow the distal end 211 to be advanced and retracted in fixed intervals 217. Advantageously, three detents 216 are formed with intervals 217 therebetween of approximately 2 mm, allowing the distal end 211 to be advanced to a maximum length 218 of approximately 6 mm. Preferably, the channel 214 supporting the distal end 211 has a length 219 at least equal to the maximum length 218. It will be appreciated that the probe 210 reduces the need for separate probes having differently dimensioned distal ends.

Figure 32:
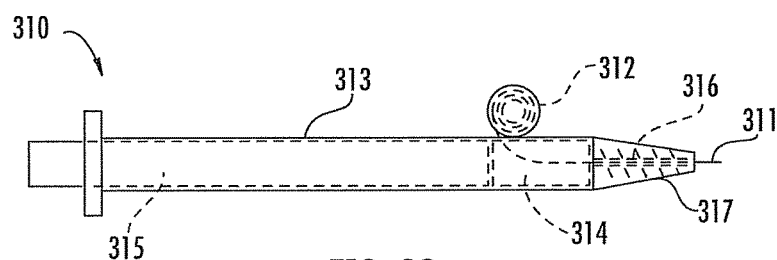
FIG. 32 is a schematic side view of a probe having a spool of wire advanceable to replace a damaged distal end and a plunger to advance the distal end, with hidden components shown in broken lines.

In an additional embodiment (FIG. 32), a probe 310 has a distal end 311 connected to a wire spool 312. Within a probe body 313, wire from the spool 312 is routed through a fixation element 314, which is rearwardly biased against a plunger 315 by a spring 316. The spring 316 is arranged in a cap 317 that is releasably connected, for instance by a threaded joint, to the body 313, allowing easier access to the wire.

The distal end 311 is threaded through the fixation element 314 to the end of the cap 317 by feeding wire from the spool 312. A thumb wheel or other operation may advantageously be provided for the spool 312. The fed wire is secured within the fixation element 314. The plunger 315 is then operable to engage the fixation element 314 to advance the distal end 311 to a desired length. Preferably, the plunger 315 is operable in cooperation with the body 313 to advance the distal end 311 in fixed intervals. It will be appreciated that the probe 310 reduces the need to dispose of a probe when its distal end becomes bent or otherwise rendered unsuitable for continued use. Instead, the unsuitable portion can be cut off and the wire advanced to form a new distal end.

In the embodiment illustrated in FIGS. 2-4, 8, and 9, the probe 20 can have a longitudinal lumen 21 therethrough, with a plurality of distal holes 22 through the probe wall 23 in fluid communication with the lumen 21, as well as a tapered tip 24. The lumen 21 can be used in concert with a source of suction 25 (FIG. 9) for removing contents 26 from the meibomian gland 13, and/or with a source of a fluid and pumping means 27 (FIG. 8), for injecting a substance 28 into the meibomian gland 13. For probes having longitudinal lumens, polyimid tubes have been found satisfactory.

In order to provide stability to the probe 10, an apparatus may be contemplated for supporting the probe 10. For example, in the apparatus 30 illustrated in FIG. 10, an articulated arm 31 is affixed to a base 32, the arm 31 having a clamp 33 at a distal end 37 for releasably holding the probe 10. A patient head rest 34 retains the eye 35 in a stable position, and the physician can visualize the eyelid 35 and probe 10 through visualization optics, for example, a scope 36, which are positioned on an opposite side of the probe 10 from the patient eyelid 35.

Figure 11:
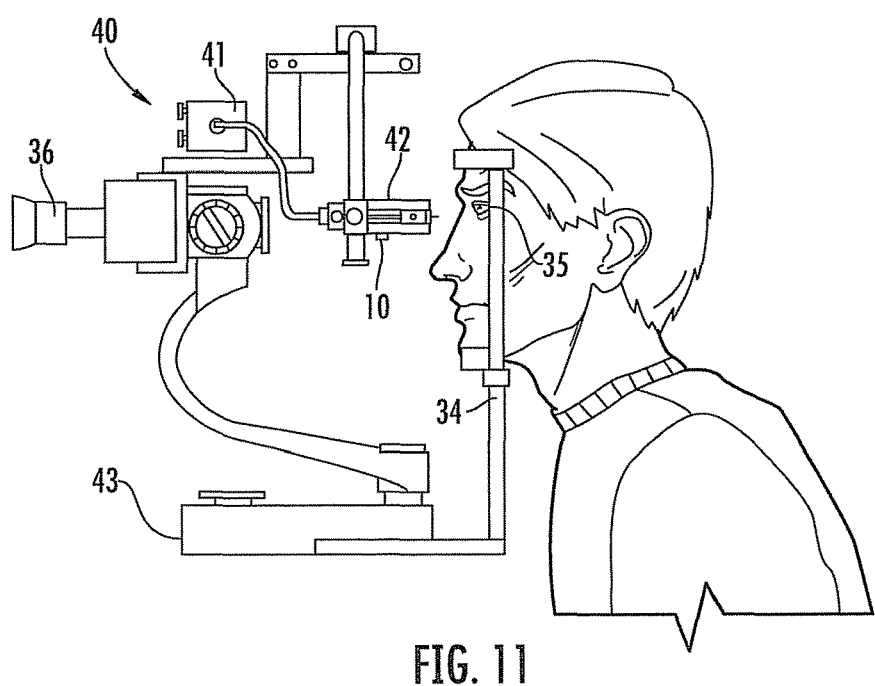
FIG. 11 is a side perspective view of an automated instrument for supporting and guiding a probe with a pump for aspiration and/or delivery.
Figure 12:
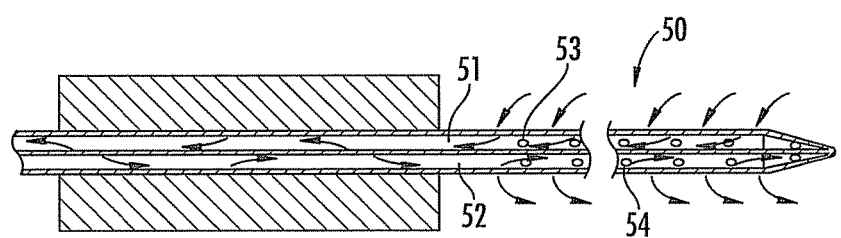
FIG. 12 is a side cross-sectional view of a probe having a double lumen for performing both aspiration and fluid delivery.
Figure 13:
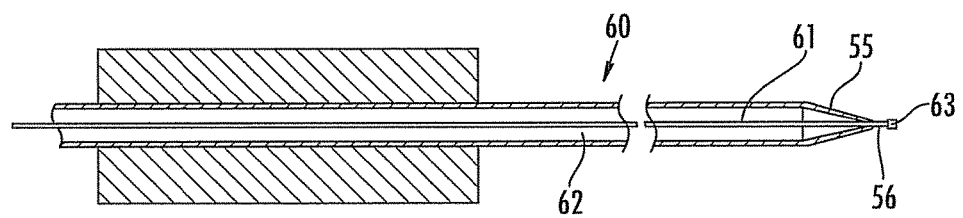
FIG. 13 is a side cross-sectional view of a probe having a movable element therein.
Figure 14:
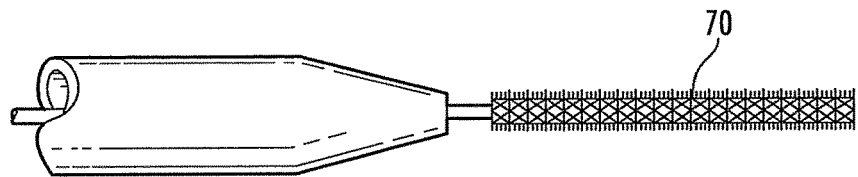
FIGS. 14-18 are side cross-sectional views of alternate embodiments of probe tips.
Figure 15:
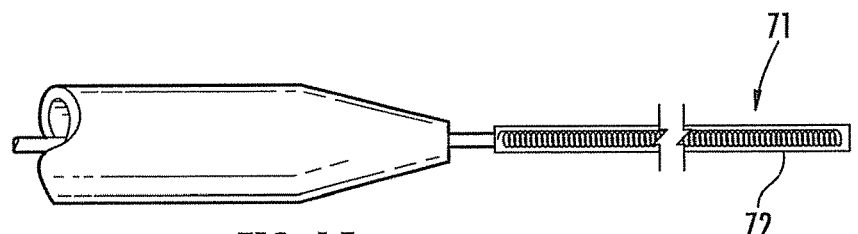
Figure 16:
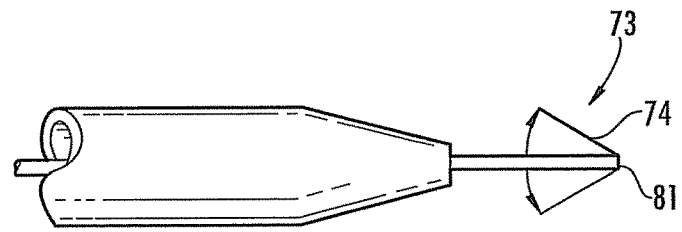
Figure 17:
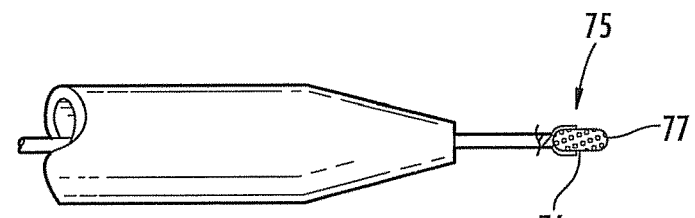

In another apparatus 40 illustrated in FIG. 11, a motion-producing element such as a motor 41 driven automated support 42 is affixed to a base 43, and is controllable by a user. The motion imparted to the probe 10 is preferably substantially linear, and, once the user has ascertained that the probe tip 11 is aligned with the gland orifice 12, the motor 41 can be activated to impel the probe 10 into the meibomian gland 13. The other elements can be substantially the same as in FIG. 10.

Visualization can also be enhanced with the use of cross-illumination on the lower lid, for either manual insertion of the probe 10 or insertion using the apparatus 30 or 40. Cross-illumination of the lower lid can also aid in determining whether a given meibomian gland has atrophied, such there is, effectively, no gland to penetrate.

In another embodiment, a probe 50 (FIG. 12) includes a double lumen 51,52 running axially therealong. The first lumen 51 can be used for aspiration through a first distal hole 53 in fluid communication therewith, while the second lumen 52 can be used for injection of a fluid through a second distal hole 54 in fluid communication therewith.

A further embodiment 60 (FIG. 13) includes an elongated element 61 movable within the probe lumen 62 a distal section 56 of which is adapted to protrude out from the probe's distal end 55. The movable element 61 can have an enlarged tip 63 to assist in removing obstructions, which can protrude out from the probe distal end 55. In a similar embodiment, a probe 65 (FIG. 29) having a double lumen 66,67 can have a movable element 68 in one of the lumina 66, with the second lumen 67 having apertures 69 in communication therewith.

It may be contemplated by one of skill in the art that a plurality of probe tip embodiments may be encompassed by the present invention. The probe tip embodiments can comprise an obstruction-removing element useful for, for example, dislodging debris from the meibomian gland when the probe is moved therewithin.

Figure 18:
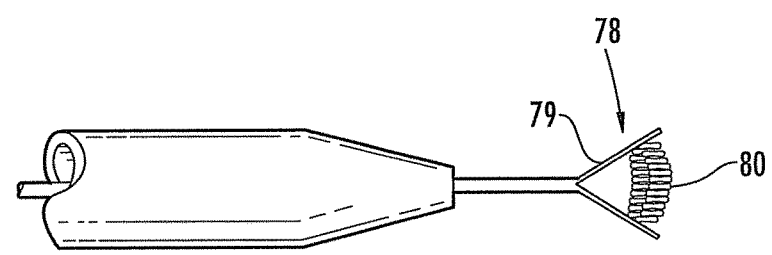

The probe tip embodiments can include, but are not intended to be limited to, an exfoliating tip 70 (FIG. 14), a tip 71 having a heating element 72 (FIG. 15), a tip 73 having a router 74 articulated at a distal end 81 (FIG. 16), a tip 75 having a gripper 76 for holding a releasing a medication-delivery element such as a pill 77 (FIG. 17), and a tip 78 having a gripper 79 for delivering a compressible, substantially toroidal stent 80 (FIG. 18). In connection with some or all of these tips, particularly, the exfoliating and routing tips, a means for imparting vibratory motion can be coupled with the tip. Vibration at ultrasonic frequencies can also be employed.

Figure 19:
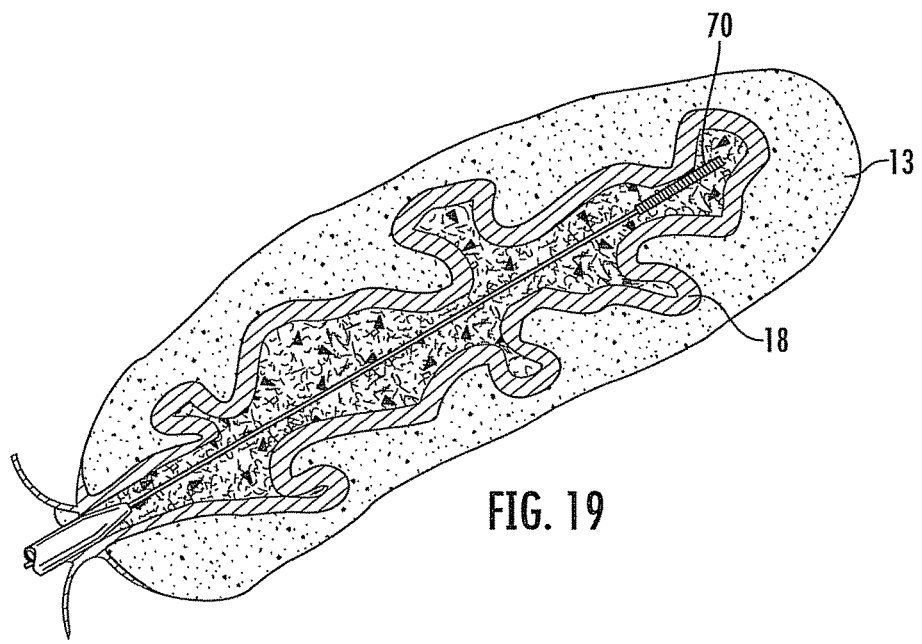
FIGS. 19 and 20 are side cross-sectional views of a meibomian gland illustrating the use of an exfoliating probe.
Figure 20:
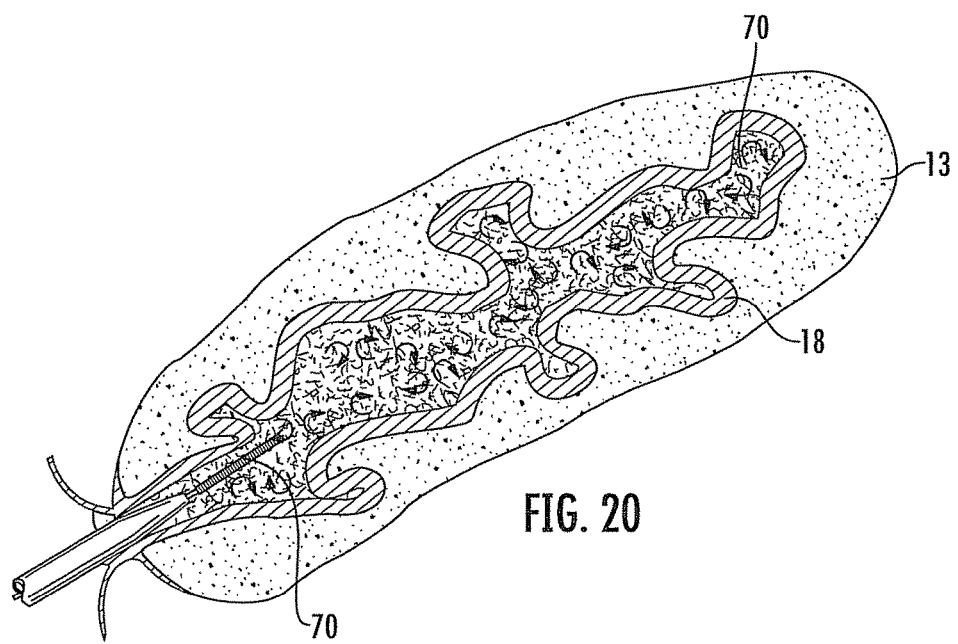
Figure 21:
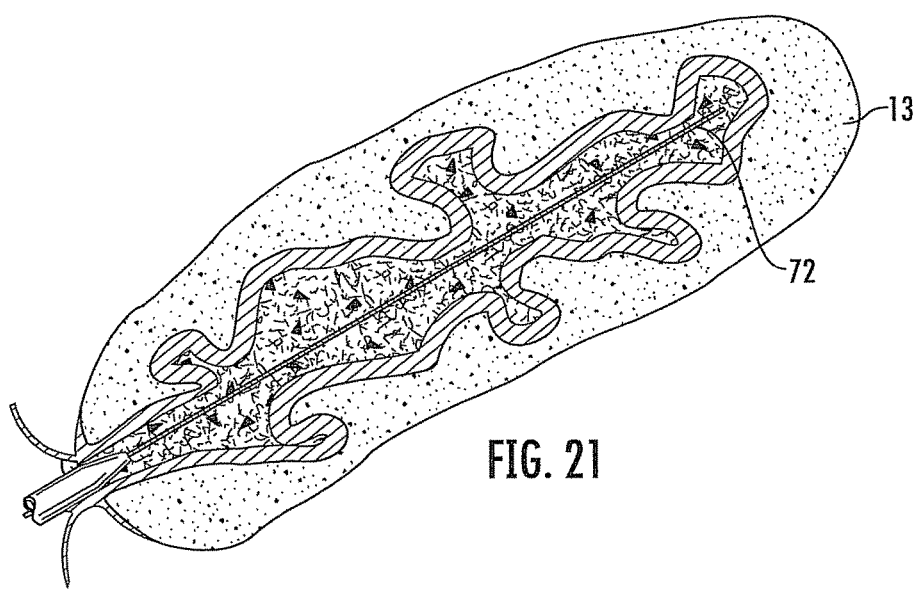
FIGS. 21 and 22 are side cross-sectional views of a meibomian gland illustrating the use of a heating element.
Figure 22:
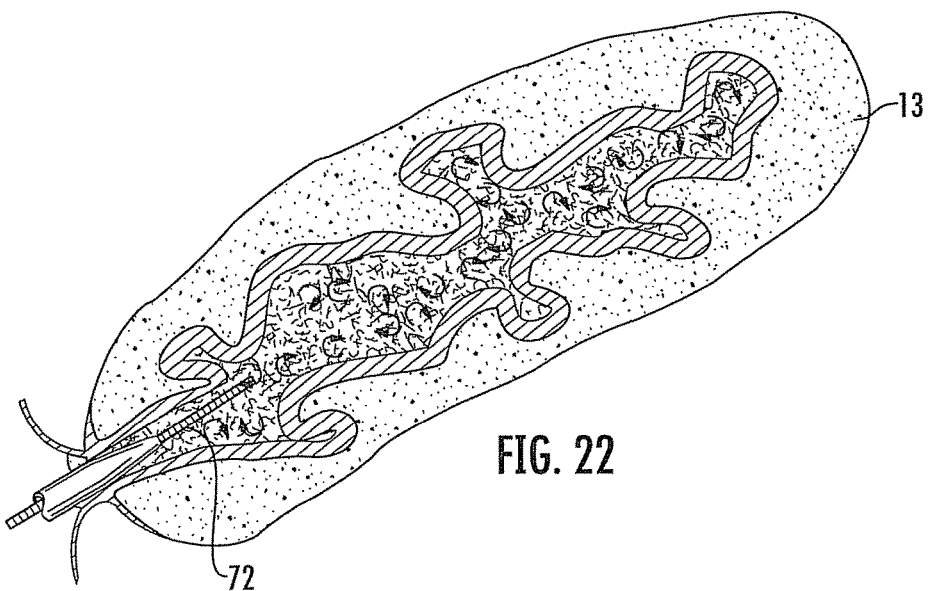
Figure 23:
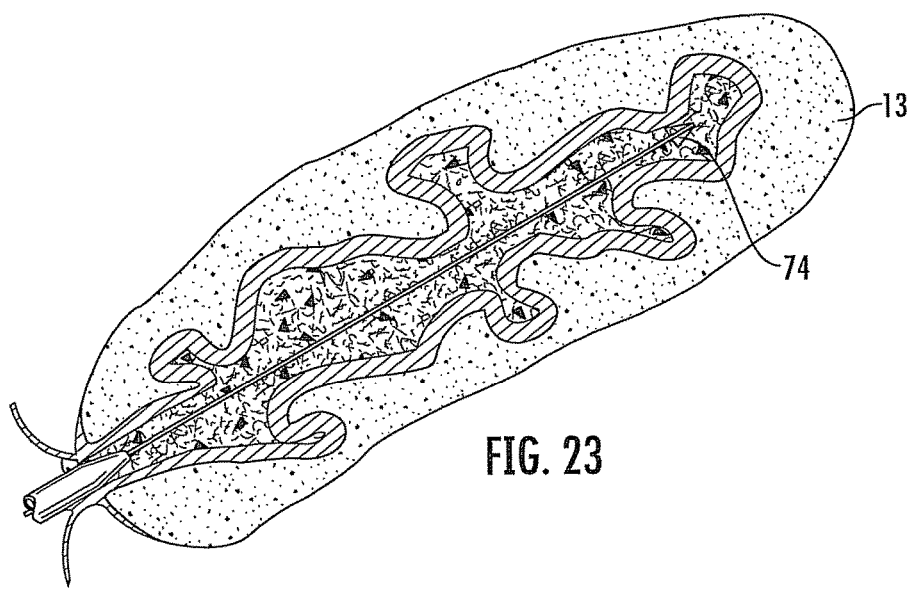
FIGS. 23 and 24 are side cross-sectional views of a meibomian gland illustrating the use of a "scoop"-type probe.
Figure 24:
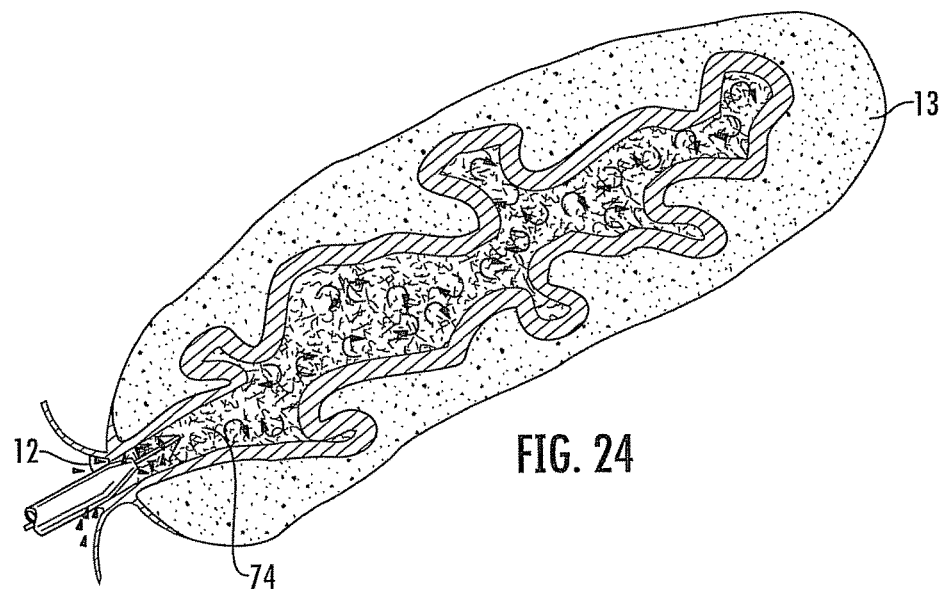
Figure 25:
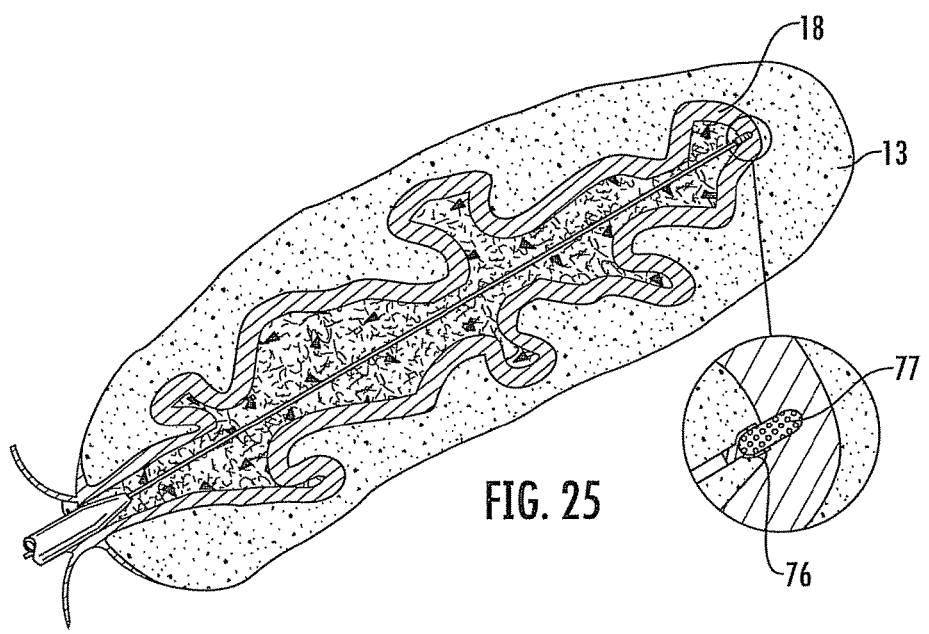
FIGS. 25 and 26 are side cross-sectional views of a meibomian gland illustrating the placement of a delivery element therein.
Figure 26:
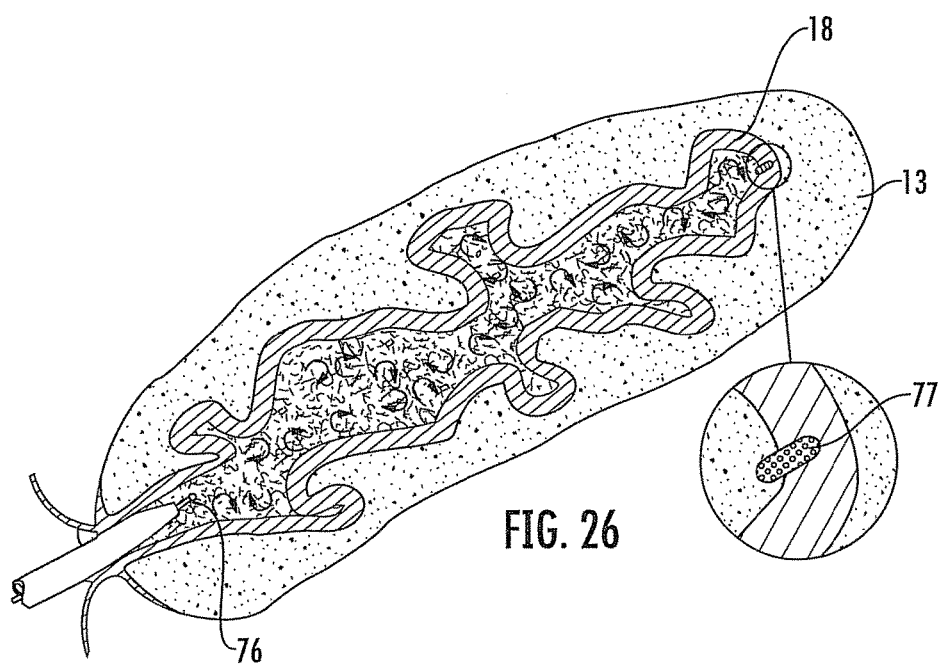
Figure 27:
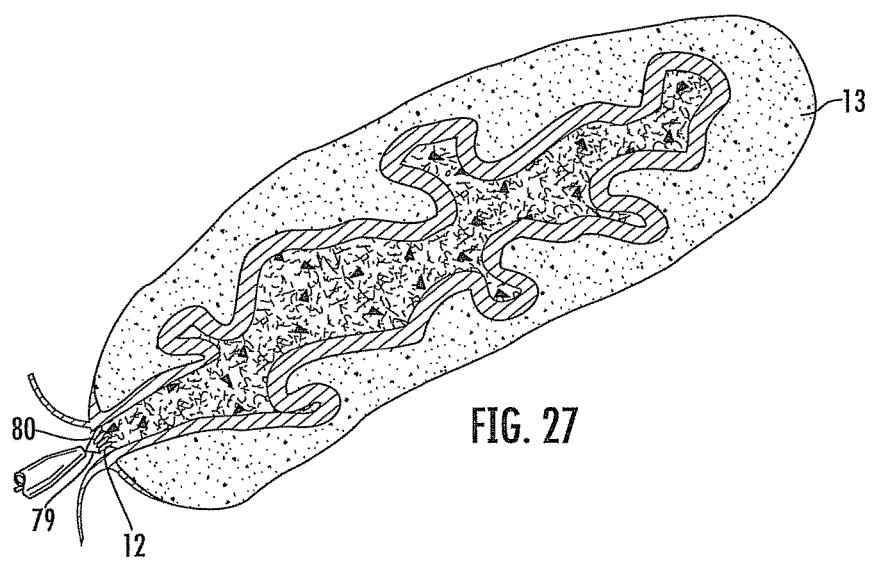
FIGS. 27 and 28 are side cross-sectional views of a meibomian gland illustrating the use of a stent-delivery probe.
Figure 28:
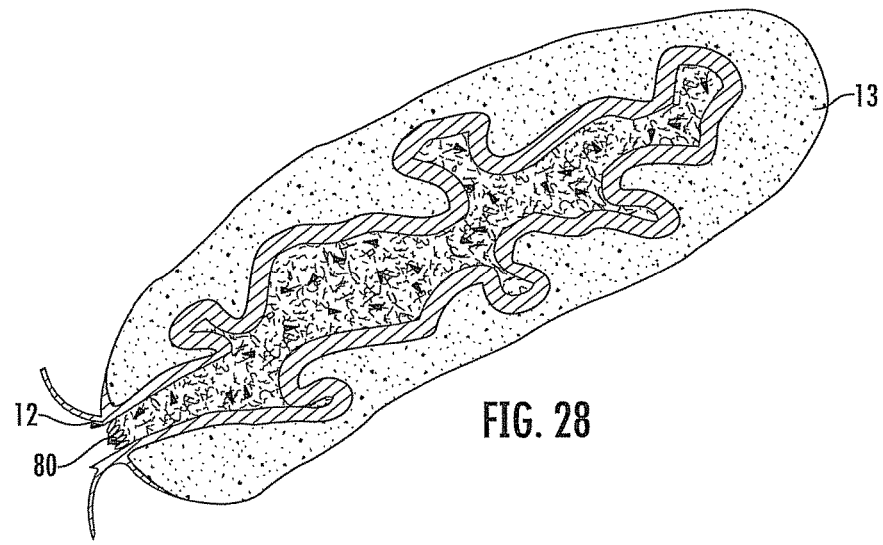
Figure 29:
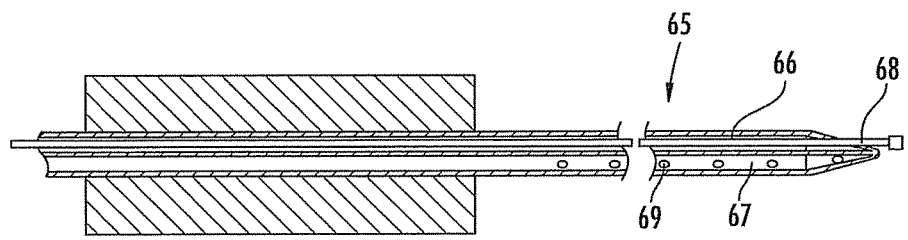
FIG. 29 is a side cross-sectional view of a probe having a double lumen and a movable element in one of the lumina.

The uses of these tips are illustrated in FIGS. 19-28. In FIGS. 19 and 20, the exfoliating tip 70 is shown loosening material from the gland wall 18; in FIGS. 21 and 22, the heating element 72 is used to release contents by reducing fluid viscosity; in FIGS. 23 and 24, the router 74 is expanded to scrape debris out the orifice 12; in FIGS. 25 and 26, the gripper tip 76 is used to deliver a pill 77 to the gland wall 18, which can contain such materials as, but not intended to be limited to, medication, stem cells, solvents, growth factors, nutrients, vitamins, hormones, genetic vectors, a nanotechnological element, or a radioactive substance for treating sebaceous cell or other type of cancer. In FIGS. 27 and 28, the stent-delivery tip 79 is illustrating as holding the stent 80 in a compressed condition and leaving in place the stent 80, which will expand for assisting in keeping the orifice 12 in an open position.

It can be seen that the various embodiments of probes disclosed herein are useful for a plurality of purposes, including those outlined above and diagnostic cytology, brachytherapy, and light-activated fluorescence for treating cancer.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus and method illustrated and described herein are by way of example, and the scope of the invention is not limited to the exact details of construction or use.

Having now described the invention, the construction, the operation and use of preferred embodiments thereof, and the advantageous new and useful results obtained thereby, the new and useful constructions, and reasonable mechanical equivalents thereof obvious to those skilled in the art, are set forth in the appended claims.

What is claimed is:

1. A method for improving meibomian gland function in a patient comprising:
    inserting a distal end of an elongated probe into a meibomian gland of an eyelid of a patient via a natural orifice thereinto.

2. The method recited in claim 1, wherein the probe has a longitudinal lumen extending therealong defined by a probe wall and a distal hole through the probe wall in fluid communication with the lumen, the distal hole positioned in the probe distal end.

3. The method recited in claim 2, further comprising applying suction to the probe lumen, for aspirating debris from the meibomian gland into the probe lumen.

4. The method recited in claim 2, further comprising injecting a fluid into the meibomian gland from the probe lumen and out through the distal hole, the fluid comprising a desired medication.

5. The method recited in claim 4, further comprising a pump element for performing the fluid injection.

6. The method recited in claim 4, wherein the desired medication includes a growth-inhibiting agent.

7. The method recited in claim 6, wherein the growth-inhibiting agent includes at least one of a fibrous tissue growth-inhibiting agent and a vascular tissue growth inhibiting agent.

8. The method recited in claim 2, wherein the distal hole comprises a plurality of distal holes.

9. The method recited in claim 1, further comprising, prior to inserting the probe:
supporting the probe with an apparatus comprising:
a base;
an articulated arm affixed to the base;
a clamp affixed to the arm positionable in approximate alignment with an eye of the patient and adapted for releasably supporting the probe; and
visualization optics affixed to the base on an opposite side of the probe from the patient; and
visualizing the patient eye through the visualization optics.

10. The method recited in claim 1, further comprising, prior to inserting the probe:
supporting the probe with an apparatus comprising:
a base;
an arm affixed to the base;
a probe support affixed to the arm, positionable in approximate alignment with the patient meibomian gland orifice, and adapted for movably and releasably supporting the probe;
a motion-producing element affixed to the base in operative communication with the probe support, adapted for causing substantially linear movement by the probe; and
visualization optics affixed to the base on an opposite side of the probe from the patient; and
visualizing the patient eye through the visualization optics; and wherein:
inserting the probe comprises:
aligning a distal tip of the probe with a target meibomian gland orifice; and
activating the motion-producing element to impel the probe into the meibomian gland via the orifice.

11. The method recited in claim 2, wherein:
the probe lumen comprises a first lumen and a second lumen;
the distal hole comprises a first distal hole in fluid communication with the first lumen and a second distal hole in fluid communication with the second lumen;
the suction is applied to the first lumen; and
further comprising injecting a fluid into the meibomian gland from the second lumen and out through the second distal hole, the fluid comprising a desired medication.

12. The method recited in claim 2, wherein the probe has an obstruction-removing element adjacent the probe distal end adapted for dislodging debris from the meibomian gland, and the method further comprises moving the obstruction-removing element within the meibomian gland to dislodge debris from the meibomian gland.

13. The method recited in claim 12, wherein the obstruction-removing element comprises a heating element.

14. The method recited in claim 12, wherein the obstruction-removing element comprises the probe distal end having an abrasive surface for exfoliating the meibomian gland.

15. The method recited in claim 12, wherein the obstruction-removing element comprises a router articulated at a distal end, and further comprising, following inserting the probe distal end, opening the router and moving the probe in a proximal direction, for scraping the meibomian gland.

16. The method recited in claim 2, wherein the probe has an elongated element positioned at least partially within the probe lumen and movable relative thereto to protrude from the probe distal end, the method further comprising moving the elongated element in a distal direction so that a distal portion of the elongated element protrudes from the probe distal end.

17. The method recited in claim 16, wherein the elongated element comprises a distal tip having a diameter greater than a diameter proximal thereof for assisting in obstruction removal.

18. The method recited in claim 16, wherein:
the probe lumen comprises a first lumen and a second lumen;
the distal hole comprises a first distal hole in fluid communication with the first lumen and a second distal hole in fluid communication with the second lumen; and
the elongated element is positioned within the first lumen; and further comprising:
applying suction to the second lumen, for aspirating debris from the meibomian gland.

19. The method recited in claim 16, further comprising releasing a medication-delivery element into the meibomian gland from adjacent the probe distal end.

20. The method recited in claim 16, further comprising positioning a structural support within the meibomian gland adjacent the orifice, for retaining the orifice in an unobstructed condition.

21. The method recited in claim 20, wherein:
the structural support comprises a compressible, substantially toroidal element; and
the elongated element comprises a gripper operable from external the meibomian gland adapted for releasably holding the toroidal element in a compressed condition, a release of the toroidal element from the gripper permitting the toroidal element to expand and assist in holding the orifice open.

22. The method recited in claim 1, wherein none of thermal energy, electromagnetic energy, and other radiation is applied proximate to the distal end during insertion into the meibomian gland.

23. The method recited in claim 22, further comprising applying at least one of thermal and electromagnetic energy proximate to the distal end after insertion into the meibomian gland.

24. The method recited in claim 1, further comprising removing the distal end of the elongated probe from the meibomian gland and subsequently inserting into the meibomian gland a wider distal end.

25. The method recited in claim 1, further comprising removing the distal end of the elongated probe from the meibomian gland and subsequently inserting into the meibomian gland a longer distal end.

* * * * *